United States Patent
Schwarz et al.

(10) Patent No.: US 11,331,167 B2
(45) Date of Patent: May 17, 2022

(54) IMPLANT SYSTEM WITH HYDROXYLATED SOFT TISSUE CONTACT SURFACE

(71) Applicant: STRAUMANN HOLDING AG, Basel (CH)

(72) Inventors: Frank Schwarz, Dusseldorf (DE); Jürgen Becker, Dusseldorf (DE); Marco Wieland, Basel (CH); Michel Dard, Lestal (CH)

(73) Assignee: STRAUMANN HOLDING AG, Basel (CH)

(*) Notice: Subject to any disclaimer, the term of this patent is extended or adjusted under 35 U.S.C. 154(b) by 689 days.

(21) Appl. No.: 16/224,304

(22) Filed: Dec. 18, 2018

(65) Prior Publication Data
US 2019/0117344 A1 Apr. 25, 2019

Related U.S. Application Data

(63) Continuation of application No. 11/680,055, filed on Feb. 28, 2007, now abandoned.

(30) Foreign Application Priority Data
Feb. 28, 2006 (EP) .................... 06004063

(51) Int. Cl.
| | | |
|---|---|---|
| A61C 8/00 | (2006.01) | |
| A61L 27/50 | (2006.01) | |
| A61K 6/30 | (2020.01) | |
| B65D 85/50 | (2006.01) | |

(52) U.S. Cl.
CPC ............ *A61C 8/0013* (2013.01); *A61C 8/005* (2013.01); *A61C 8/0009* (2013.01); *A61C 8/0012* (2013.01); *A61C 8/0015* (2013.01); *A61C 8/0093* (2013.01); *A61K 6/30* (2020.01); *A61L 27/50* (2013.01); *B65D 85/50* (2013.01); *A61C 2008/0046* (2013.01); *A61L 2400/18* (2013.01); *A61L 2430/12* (2013.01)

(58) Field of Classification Search
CPC ............................................... A61C 8/00–0098
See application file for complete search history.

(56) References Cited

U.S. PATENT DOCUMENTS

| | | |
|---|---|---|
| 3,797,113 A | 3/1974 | Brainin |
| 4,955,536 A | 9/1990 | Foller et al. |
| 4,995,553 A | 2/1991 | Foller et al. |

(Continued)

FOREIGN PATENT DOCUMENTS

| | | |
|---|---|---|
| FR | 2623709 A1 | 6/1989 |
| FR | 2636709 B1 | 3/1990 |

(Continued)

OTHER PUBLICATIONS

Wieland, Marco, "Soft Tissue Attachment," Jul. 3, 2008, Straumann AG, Basel, Switzerland.

(Continued)

*Primary Examiner* — Yogesh P Patel
(74) *Attorney, Agent, or Firm* — Oliff PLC

(57) ABSTRACT

Two part implant for attachment of artificial teeth comprising a base body having a bone contact surface and a soft tissue contact surface. The soft tissue contact surface is at least partially hydroxylated or silanated which results in an improved soft tissue integration.

15 Claims, 2 Drawing Sheets

(56) References Cited

U.S. PATENT DOCUMENTS

| | | | |
|---|---|---|---|
| 5,205,745 A * | 4/1993 | Kamiya | A61C 8/0022 433/173 |
| 5,571,017 A | 11/1996 | Niznick | |
| 5,588,838 A | 12/1996 | Hansson et al. | |
| 5,642,996 A | 7/1997 | Mochida et al. | |
| 6,095,817 A | 8/2000 | Wagner et al. | |
| 6,261,097 B1 * | 7/2001 | Schmutz | A61C 8/0087 433/173 |
| 6,702,855 B1 * | 3/2004 | Steinemann | A61L 27/06 623/23.53 |
| 6,726,481 B1 | 4/2004 | Zickmann et al. | |
| 7,662,190 B2 | 2/2010 | Steinemann et al. | |
| 2003/0104338 A1 | 6/2003 | Cottrell | |
| 2004/0180308 A1 | 9/2004 | Ebi et al. | |
| 2004/0210309 A1 | 10/2004 | Denzer et al. | |
| 2005/0037319 A1 | 2/2005 | Bulard et al. | |
| 2005/0064007 A1 | 3/2005 | Steinemann et al. | |
| 2005/0106534 A1 | 5/2005 | Gahlert | |
| 2005/0113834 A1 * | 5/2005 | Breitenstien | A61L 27/30 606/331 |

FOREIGN PATENT DOCUMENTS

| | | | |
|---|---|---|---|
| WO | 00/44305 A1 | 8/2000 | |
| WO | 03/039390 A1 | 5/2003 | |
| WO | 03/045268 A1 | 6/2003 | |

OTHER PUBLICATIONS

Schwarz, et al., "Histological and immunohistochemical analysis of initial and early subepithelial connective tissue attachment at chemically modified and conventional SLA® titanium implants. A pilot study in dogs," Clin Oral Invest, 2007, 11:245-255, Springer.

Schwarz, et al., "Effects of Surface Hydrophilicity and Microtopography on Eady Stages of Soft and Hard Tissue Integration at Non-submerged Titanium Implants: An Immunohistochemical Study in Dogs," J. Periodontal, Nov. 2007, vol. 78, No. 11, 2171-2184.
Aug. 1, 2017 Office Action issued in U.S. Appl. No. 14/474,604.
Feb. 23, 2018 Office Action issued in U.S. Appl. No. 14/474,604.
Sep. 18, 2018 Office Action issued in U.S. Appl. No. 11/680,055.
Aug. 28, 2018 Office Action issued in U.S. Appl. No. 14/474,604.
Oct. 6, 2016 Office Action issued in U.S. Appl. No. 11/680,055.
May 12, 2017 Office Action issued in U.S. Appl. No. 11/680,055.
Dec. 20, 2017 Office Action issued in U.S. Appl. No. 11/680,055.
Feb. 7, 2017 Office Action issued in U.S. Appl. No. 14/474,604.
Meyer, M., "Hydroxylapatitbeschichtung fur perkutane Silicon— und Titanimplantate", TU Berlin, Sep. 22, 2003.
May 31, 2006 Search Report issued in European U.S. Appl. No. 06/004,063.
Mar. 28, 2016 Office Action Office Action issued in U.S. Appl. No. 11/680,055.
Oct. 6, 2015 Office Action issued in U.S. Appl. No. 11/680,055.
Sep. 4, 2014 Office Action issued in U.S. Appl. No. 11/680,055.
Feb. 5, 2014 Office Action issued in U.S. Appl. No. 11/680,055.
Aug. 22, 2013 Office Action issued in U.S. Appl. No. 11/680,055.
Mar. 26, 2013 Office Action issued in U.S. Appl. No. 11/680,055.
Oct. 30, 2012 Office Action issued in U.S. Appl. No. 11/680,055.
Apr. 13, 2012 Office Action issued in U.S. Appl. No. 11/680,055.
Nov. 7, 2011 Office Action issued in U.S. Appl. No. 11/680,055.
Jun. 9, 2011 Office Action issued in U.S. Appl. No. 11/680,055.
Dec. 17, 2010 Office Action issued in U.S. Appl. No. 11/680,055.
Jul. 8, 2010 Office Action issued in U.S. Appl. No. 11/680,055.
Jan. 15, 2010 Office Action issued in U.S. Appl. No. 11/680,055.
Jun. 12, 2009 Office Action issued in U.S. Appl. No. 11/680,055.
Oct. 27, 2008 Office Action issued in U.S. Appl. No. 11/680,055.
Jan. 23, 2008 Office Action issued in U.S. Appl. No. 11/680,055.

* cited by examiner

IMPLANT SYSTEM WITH HYDROXYLATED SOFT TISSUE CONTACT SURFACE

The present application is a continuation of U.S. application Ser. No. 11/680,055, filed Feb. 28, 2007, which in turn claims priority to European Patent Application No. 06004063.1, filed Feb. 28, 2006. The disclosure of the prior applications is hereby incorporated by reference herein in its entirety.

TECHNICAL FIELD

The present invention relates to a two-stage implant comprising a base body having a bone contact surface and a tissue contact surface and to a method for preparing such an implant.

BACKGROUND

Implants which are used for insertion into bone, for example for attachment of artificial teeth are known per se. Different types of implant systems are known, for example two-part implant systems. Said two-part implant systems comprise first an anchoring part for anchoring within the bone and second a mounting part. Onto the mounting part prosthesis elements, such as bridges or crowns, are screwed or cemented usually using intermediate so-called abutments.

A central property of said implants is their osteointegration time, that is to say the time that passes before the bone substance has become connected with sufficient strength and permanently to the bone contact surface, that is to say it has become integrated with it. much effort has been made in order to improve the osteointegration of said implants, such as described in EP 1 150 620. It was shown that the osteointegration time was significantly shorter if the bone contact surface of the implant is roughened, hydroxylated and hydrophilic.

US 2004/0049287 discloses an endosseous implant, said implant having a surface made from metal or ceramic. The surface has a smooth or rough texture and has been treated with at least one pharmaceutically acceptable organic compound carrying at least one phosphonic acid group. Said implants showed an improved bone bonding strength.

U.S. Pat. No. 5,397,362 discloses an implant prosthesis comprising a substrate of a ceramic material, a glass layer coated over the adhering interface of the substrate and a thermally sprayed layer of calcium phosphate based material formed over the glass layer.

WO 2005/120386 discloses a dental implant comprising an anchoring element for anchoring the dental implant in the bone and an abutment for fastening a crown or the like suprastructure. The anchoring element and the abutment are produced from zirconium oxide.

However, there is considerable evidence supporting the view that the supracrestal connective tissue plays a fundamental role in establishing an effective seal between the oral environment and the endosseous part of a dental implant. Indeed, the presence of bacteria on the implant surface may lead to an inflammation of the peri-implant mucosa, and, if left untreated, the inflammation spreads apically and results in bone resorption. As a consequence of the fact that rough surfaces accumulate and retain more plaque than smooth surfaces, nowadays, the soft tissue contact surface of the implants is highly polished (see Oral Implantology, Thieme Verlag, 1996, page 438).

Various experiments have been carried out to investigate the difference of early inflammatory response to mucosa-penetrating implants prepared with varying surface roughness. Despite the fact that a rough surface may accumulate greater amounts of plaque than a smooth surface, no relation was found between inflammatory response and implant surface roughness (Wennerberg et al, J. Clin. Periodontol 2003: 30: 88-94; Quirynen et al, The International Journal of Oral and Maxillofacial Implants, 11, No. 2, 1996).

It is the problem of the present invention to provide an implant with improved soft tissue integration.

SUMMARY

Surprisingly it was found that an implant comprising a base body having a bone contact surface and a soft tissue contact surface, wherein the soft tissue contact surface is at least partially hydroxylated or silanated. Said soft tissue contact surface has the potential to promote formation of soft tissue attachment. In contrast to conventional implants having a roughened, in some cases also hydroxylated bone contact surface and a smooth unhydroxylated tissue contact surface, the implant according to the present invention leads to the formation of new connective tissue adjacent to the soft tissue contact surface of the implant and tends to be in close contact with the soft tissue contact surface of the implant. The loose connective tissue seems to become organized and replaced be newly formed collagen fibers, originating from its outer zone. These fibers tend to be organized in a perpendicular way towards the soft tissue contact surface, similarly to the naturally occurring fibers most responsible for compensation forces on the tooth.

An implant in terms of the present invention is intended to mean the anchor part of a two-part implant system, that is that part which becomes integrated with the bone. Said anchoring part is sunk in up to about 1.5-3 mm above the bone ridge at mucosal level. Said anchor part has a bone contact surface meaning the part which is in contact with the bone. The top of the anchoring part which is in contact with the soft tissue is defined as soft tissue contact surface. After implantation the wound edges can be directly adapted to the soft tissue contact surface thereby effecting a primary soft tissue closure to the implant.

"Hydroxylated" in terms of the present invention means hydroxyl groups which are present in the outermost atomic layer of the implant surface. If the implant comprises titanium, zirconium, tantalum, niobium, hafnium or alloys thereof as well as chemically similarly reacting alloys, it is assumed that the surface of titanium metal oxidizes spontaneously in air and water and that a reaction then takes place with water on the surface to form hydroxyl groups. This surface containing hydroxyl groups is referred to in the literature as a "hydroxylated" surface; cf. H. P. Boehm, Acidic and Basic Properties of Hydroxylated Metal Oxide Surfaces, Discussions Faraday Society, vol. 52, 1971, pp. 264-275. The same applies to ceramic surfaces (either on a ceramic implant or a metallic implant with a ceramic coating). A metal surface whose hydroxyl groups are covalently blocked, e.g. because of chemical modification, is not a "hydroxylated" surface in terms of the present invention.

Silanated in terms of the present invention means that the implant surface is covered by a silanole or by an organo silane compound which has at least one free hydroxyl group. Examples of such organo silane compounds are $X_nSiR_{4-n}$, wherein X is selected from the group consisting of Cl, Br, I, F or OR, and R is selected from the group of lower alkyl groups, such as methyl, ethyl, propyl etc. Implants made of ceramic are preferably covered by an organo silane compound, whereas implants made of ceramic are preferably covered by an organo silane compound. Implants made of metal can also be covered by an organo silane compound and implants made of ceramic can also be covered by silanole.

In a preferred embodiment of the present invention the soft tissue contact surface is completely hydroxylated. Such an implant showed good results in vivo and said implants are economically interesting and can be produced in a controlled process. In addition it has been shown that with the implants according to the present invention the healing process is improved, that is a good osteointegration as well as an excellent soft tissue integration. Therefore, the implants comprise a reduced risk of periimplantitis and as a consequence fewer implants will have to be replaced. Due to their inorganic purity, meaning that the soft tissue contact surface is free of organic compounds, the surface charge is better available. Therefore, the surface is hydrophil, which results in an improved soft tissue integration. Therefore, they do not bear the risk of autoimmune reactions and other unwanted side effects.

In a further embodiment of the present invention the soft tissue contact surface is roughened and hydroxylated. A roughened surface in terms of the present invention means a macroscopic texture of the surface which is obtained for example by sandblasting the soft tissue contact surface. It has been found that if the soft tissue contact surface is roughened and hydroxylated the blood coagulum is stabilized which accelerates the healing procedure.

In a further embodiment of the present invention the soft tissue contact surface is smooth but hydroxylated. A smooth surface in terms of the present invention means a macroscopic texture of the surface which is obtained for example by machining or additional polishing, preferably by electropolishing the soft tissue contact surface. With a smooth surface the accumulation of plaque can be prevented or at least minimized, and such a soft tissue contact surface has outstanding wettability properties which is highly preferred.

In a further embodiment of the present invention the bone contact surface and the soft tissue surface of the implant are both roughened, hydroxylated and hydrophilic or alternatively both smooth, hydroxylated and hydrophilic. Such implants are particularly easy to produce since the entire implant can be treated in the same way. This is a very big advantage and is based on the surprising finding that a hydroxylated, hydrophilic, and roughened or smooth soft tissue surface of the implant shows improved soft tissue integration.

In a further preferred embodiment of the present invention the soft tissue contact surface is hydrophilic. In terms of the present invention, the soft tissue contact surface is referred to as "hydrophilic" if it is freely accessible to the body fluid and not covered with foreign substances, for example substances with a hydrophobic action. Various volatile hydrocarbons are conventionally present in non-purified air. These are rapidly adsorbed in a thin layer by hydroxylated and hydrophilic surfaces, whereby such surfaces are no longer hydrophilic. Likewise, such a hydroxylated and hydrophilic surface can become hydrophobic if the hydroxyl groups present on the surface associate or react chemically e.g. with carbon dioxide present in the air or with organic solvents, such as methanol or acetone, introduced via the cleaning process. The hydrophilic properties of the soft tissue contact surface may result in a higher wettability when compared to an untreated soft tissue contact surface, which promotes formation of the soft tissue. Further, the charge on the surface is better available which may accelerate the formation of soft tissue attachment as well.

The implants according to the invention preferably comprise mainly a metal selected from the group consisting of titanium, zirconium, niobium, hafnium or tantalum, preferably titanium or zirconium. Alternatively the implants comprise an alloy of metals selected from the group consisting of titanium, zirconium, niobium, hafnium or tantalum, preferably a binary titanium /zirconium alloy. Such implants, their nature and the metal materials used to produce them are known per se and are described for example in J. Black, G. Hastings, Handbook of Biomaterials Properties, pages 135-200, published by Chapman & Hall, London, 1998. From an aesthetic point of view, in particular in the front visible region, the soft tissue contact surface is preferably covered with a ceramic coating. This is for example obtainable by thermally spraying a ceramic material on the surface of a metallic core material such as described in U.S. Pat. No. 4,746,532. Also EP 1 566 152 describes the coating of a dental implant with zirconia. Alternatively the implants may comprise a ceramic ring element, in particular in the soft tissue contact surface. Such ceramic coatings and ring elements comprise typically zirconia, aluminia, silica or mixtures thereof with possible further constituents, preferably they are made of zirconia. Alternatively the implant according to the present invention may be made of ceramic.

In a most preferred embodiment the implant according to the present invention is made of ceramic comprising a zirconium oxid based material. The cubic structure of zirconium oxide (zirconia) may be stabilized by metallic oxides at room temperature. Preferred metallic oxides are magnesium oxide, calcium oxide, oxides of the lanthanide group, preferably yttrium oxide. Depending on the content of said metallic oxides the cubic high temperature phase of zirconia can be stabilized fully or partly at room temperature (cubic stabilized zirconium oxide). Preferably zirconia is stabilized by yttrium oxide.

The present invention also relates to the process for preparing the above disclosed implant.

To obtain the hydroxylated surface, the soft tissue contact surface of the implant is preferably etched with an inorganic acid, an inorganic base, a mixture of inorganic bases or a mixture of inorganic acids. Particularly preferred are inorganic acids such as hydrofluoric acid, hydrochloric acid, sulfuric acid, nitric acid or a mixture of such acids. Preferably the implant is etched with a mixture of hydrochloric acid (conc.), sulphuric acid (conc.) and water in a weight ration of about 2:1:1. Alternatively the surface is activated with hydrochloric acid (conc.), hydrogen peroxide (conc.) and water in a weight ratio of about 1:1:5. The soft tissue contact surface is then washed with pure water in an inert atmosphere.

A roughened soft tissue contact surface can be obtained by sandblasting said surface and keeping the surface in the resulting state if it is already hydroxylated and hydrophilic or converting the sandblasted surface to a hydroxylated and hydrophilic state in a separate process step.

In particular, the roughened soft tissue contact surface can be produced by shot peening or sandblasting said surface and/or roughening it by using plasma technology, and then treating the mechanically roughened surface by an electrolytic or chemical process until a hydroxylated and hydrophilic surface is formed.

The preferred procedure is to
shot-peen the soft tissue contact surface of the implant and then etch it with diluted hydrofluoric acid at room temperature; or
sandblast the soft tissue contact surface of the implant, e.g. with aluminium oxide particles having a mean size of 0.1-0.25 mm or 0.25-0.5 mm, and then treat it at elevated temperature with a hydrochloric acid/sulfuric acid mixture and wash it with pure distilled and carbon-free ($CO_2$ and other carbons) water; or sandblast the soft tissue contact surface of the implant with coarse particles, e.g. with a mixture of particles as defined above, and then treat it with a hydrochloric acid/nitric acid mixture and wash it with pure distilled and carbon-free ($CO_2$ and other carbons) water; or treat the soft tissue contact surface of the implant with a mixture of hydrochloric acid (conc.), hydrogen peroxide (conc.) and water in a weight ratio of about 1:1:5 and wash it with pure distilled and carbon-free ($CO_2$ and other carbons) water; or roughen the soft tissue contact surface by using plasma technology and then hydroxylate it in a mixture of hydrochloric acid (conc.), hydrogen peroxide (conc.) and water in a weight ratio of about 1:1:5 and wash it with pure distilled and carbon-free ($CO_2$ and other carbons) water; or treat the soft tissue contact surface by an electrolytic process, optionally after mechanical roughening of the surface, and then wash it with pure distilled and carbon-free ($CO_2$ and other carbons) water.

treat the soft tissue contact surface of the implant by plasma cleaning or UV-treatment.

These methods are known to those skilled in the art and are described for example in U.S. Pat. No. 5,071,351. The hydroxylated soft tissue contact surface of the implant is after such a treatment free of organic debris and has increased wettability. As a result, the implant becomes more intimately involved with the surrounding bone and tissue structure.

Whatever the case may be, according to the invention the implant is not subjected to further aftertreatment, i.e. it is not treated with alcohol, acetone or any other organic solvent. In particular, said pure water contains neither carbon dioxide nor hydrocarbon vapours and especially no acetone and no alcohols like methanol or ethanol. However, it can contain special additives as described below. The "pure" water used for washing has preferably been distilled several times or prepared by reverse osmosis; the water has preferably been prepared in an inert atmosphere, i.e. under reduced pressure in a nitrogen or noble gas atmosphere, for example.

Following these procedures, the implant 1 obtained is left in pure water and stored in a closed vessel or a covering 2, as shown in FIG. 2. In addition to water, the interior of the covering can contain inert gases 3, for example nitrogen, oxygen or a noble gas such as argon. The implant obtained is preferably stored in pure water optionally containing selective additives, and in a covering which is practically impermeable to gases and liquids, especially to carbon oxides, the interior of the covering being devoid of any compounds capable of impairing the activity of the implant surface.

Alternatively, the implant could be placed in an inert gas atmosphere.

The implant according to the invention, or at least its hydroxylated and hydrophilic surface, is preferably sealed in a gas-tight and liquid-tight covering, the interior of the covering being devoid of any compounds capable of impairing the biological activity of the implant surface. In this way it is avoided that the surface loses its activation fully or partially by means of air constituents, before the dental implant is applied. In a preferred embodiment there is a reducing atmosphere in the interior of the covering. This gas-tight and liquid-tight covering is preferably a heat-sealed ampoule made of glass, metal, a synthetic polymer or some other gas-tight and liquid-tight material, or a combination of these materials. The metal preferably takes the form of a thin sheet, it being possible for polymeric materials and metal sheets, as well as glass, to be combined together to form a suitable packaging in a manner known per se.

Examples of suitable additives which can be incorporated in the pure water are cations and anions which already occur in the body fluid. In order to stabilize the positive charge the implant according to the present invention is preferably stored at a pH ranging from pH 3 to 7, preferably 4 to 6. Alternatively it is also possible to store the implant at a pH ranging from pH 7 to 10 in order to stabilize the negative charge. Preferred cations are $Na^+$, $K^+$, $Mg^{2+}$ and $Ca^{2+}$. The preferred anion is $Cl^-$. The total amount of said cations or anions ranges preferably from about 50 mM to 250 mM, particularly preferably from about 100 mM to 200 mM, and is preferably about 150 mM. If the covering contains divalent cations, especially $Mg^{2+}$, $Ca^{2+}$, $Sr^{2+}$ and/or $Mn^{2+}$, on their own or in combination with the above-mentioned monovalent cations, the total amount of divalent cations present preferably ranges from 1 mM to 20 mM.

The invention is explained below on the basis of figures and illustrative embodiments, without in any way limiting the invention to the embodiments shown.

DETAILED DESCRIPTION

Figure 1:
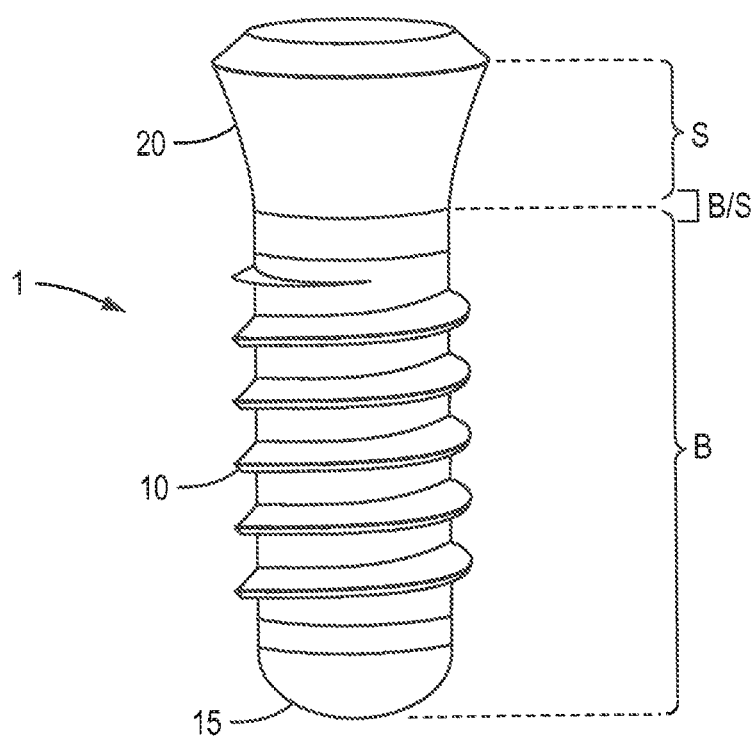
FIG. 1 shows the different areas of an embodiment of an implant according to the invention that is the anchoring part of a two-part implant system.
Figure 2:
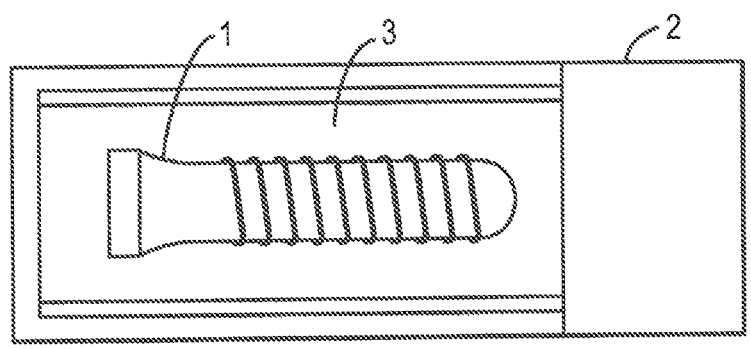
FIG. 2 shows an implant system according to the invention.

In accordance with one embodiment of the invention, FIG. 1 shows an implant 1 which is preferably made of a tissue compatible metal or of an alloy of such a metal, in particular of titanium or of a titanium alloy. Alternatively the implant is made of ceramic, preferably of zirconia. Further it is possible that parts of the implants are made of metal and parts of the implants are made of ceramic, for example if the inner part is made of titanium and the outer part of the implant is made of ceramic. The implant 1 has a threaded section 10 and a rounded lower end 15. At its upper end it has a slightly enlarged conical section. Said implant 1 is subdivided into a bone contact surface B and a soft tissue contact surface S. In the boundary area of these surfaces, there is a transition area from bone contact surface B to soft tissue contact surface S, which transition area is assigned to both aforementioned areas. The question of whether this area, in the implanted state, is located in the bone or in the soft tissue depends on a large number of factors, for example the depth to which the implant is screwed, the tissue reaction, etc. The transition area has to be treated in the same way as the bone contact surface, in order to make sure, that in any case an optimal osteointegration is ensured. In the case of implants 1 made of titanium, the bone contact surface is preferably roughened, and even more preferred hydroxylated and hydrophilic as well. The soft tissue contact surface S is at least partially, preferably completely hydroxylated. In a preferred embodiment it is also roughened and/or hydrophilic. The soft tissue contact surface of an implant according to the present invention may be made of titanium, zirconium, tantalum, niobium, hafnium or alloys thereof as well as chemically similarly reacting alloys, but it is also possible that the implant has a ceramic coating which is hydroxylated.

The Examples which follow illustrate the invention.

EXAMPLE 1

Implant with a Roughened Hydroxylated Soft Tissue Contact Surface

A common shape of dental implant in the form of a screw of diameter 4 mm and length 10 mm was produced. The crude shape was obtained in a manner known per se by removing material from the cylindrical blank by turning on a lathe and milling. The bone contact surface as well as the soft tissue surface were then sandblasted with particles having a mean size of 0.25-0.5 mm as described in EP 0 388 575. The roughened surface was then treated for about five minutes at a temperature above 80° C. with an aqueous hydrochloric acid (conc.)/sulfuric acid (conc.) mixture having an $HCl:H_2SO_4:H_2O$ ratio of 2:1:1. The implant formed in this way was washed with pure water and then heat-sealed directly in a glass ampoule filled with pure water containing 150 mM $Na^+$ ions, and the corresponding amount of $Cl^-$ anions.

To test the soft tissue integration, the above implants were placed in four female fox hounds. Each animal received 6 implants bilaterally in the upper jaw and 10 implants bilaterally in the lower jaw. The implants with a roughened hydroxylated soft tissue contact surface showed unexpectedly a much better soft tissue integration than comparable implants with an unhydroxylated surface. Soft tissue adhesion was seen already after a few days, the soft tissue integration was apparent within two weeks.

EXAMPLE 2

Implant with a Smooth Hydroxylated Soft Tissue Contact Surface

A common shape of dental implant in the form of a screw of diameter 4 mm and length 10 mm was produced. The crude shape was obtained in a manner known per se by removing material from the cylindrical blank by turning on a lathe and milling. The bone contact surface was then sandblasted with particles having a mean size of 0.25-0.5 mm, whereas the soft tissue contact surface has been electropolished. The sandblasted bone contact surface as well as the electropolished soft tissue contact surface were then treated for about five minutes at a temperature above 80° C. with an aqueous hydrochloric acid (conc.)/sulfuric acid (conc.) mixture having an $HCl:H_2SO_4:H_2O$ ratio of 2:1:1. The implant formed in this way was washed with pure water and then heat-sealed directly in a glass ampoule filled with pure water containing 150 mM $Na^+$ ions, and the corresponding amount of $Cl^-$ anions.

To test the soft tissue integration, the above implants were placed in four female fox hounds. Each animal received 6 implants bilaterally in the upper jaw and 10 implants bilaterally in the lower jaw. The implants with a smooth hydroxylated soft tissue contact surface showed unexpectedly a much better soft tissue integration than comparable implants with an unhydroxylated surface. Soft tissue adhesion was seen already after a few days, the soft tissue integration was apparent within two weeks.

The invention claimed is:

1. A method for implanting a dental implant system in a subject, comprising:
   implanting into a jaw of the subject an anchoring part of the dental implant system such that a bone contact surface of the anchoring part is in contact with bone, and a soft tissue contact surface of the anchoring part is in contact with soft tissue surrounding the bone;
   wherein:
   the soft tissue contact surface of the anchoring part is not threaded and comprises a hydroxylated or silanated surface; and
   the bone contact surface of the anchoring part comprises a threaded section.

2. The method according to claim 1, wherein the soft tissue is integrated with the soft tissue contact surface of the anchoring part after the anchoring part is implanted.

3. The method according to claim 1, wherein the anchoring part is made of a metal selected from the group consisting of titanium, zirconium, niobium, hafnium, tantalum, and alloys thereof.

4. The method according to claim 1, wherein the soft tissue contact surface is hydrophilic.

5. The method according to claim 1, wherein the soft tissue contact surface is delimited by an enlarged conical section.

6. The method according to claim 1, wherein the anchoring part widens from the bone contact surface to the soft tissue contact surface.

7. The method according to claim 1, wherein an entirety of the soft tissue contact surface is hydroxylated.

8. The method according to claim 1, wherein the soft tissue contact surface has been roughened mechanically and/or by acid etching.

9. The method according to claim 8, wherein the soft tissue contact surface has been roughened by acid etching.

10. The method according to claim 1, wherein the soft tissue contact surface and the bone contact surface have both been roughened mechanically.

11. The method according to claim 1, wherein the anchoring part is made of titanium or titanium alloy and the soft tissue contact surface has been acid-etched.

12. The method according to claim 1, wherein formation of new connective tissue adjacent to the soft tissue contact surface is promoted by the soft tissue contact surface after the anchoring part is implanted.

13. The method according to claim 1, wherein the soft tissue attaches to the soft tissue contact surface of the anchoring part to form an effective seal between an oral environment and an endosseous part of the anchoring part after the anchoring part is implanted.

14. The method according to claim 1, wherein the anchoring part is implanted in the jaw up to about 1.5 to 3 mm above a ridge of the bone at mucosal level.

15. The method according to claim 1, wherein the soft tissue contact surface and the bone contact surface of the anchoring part are both roughened, hydroxylated, and hydrophilic.

* * * * *